United States Patent [19]

Ruiz-Vela et al.

[11] Patent Number: 4,602,653
[45] Date of Patent: Jul. 29, 1986

[54] ELECTRONICALLY-CONTROLLED GAS BLENDING SYSTEM

[75] Inventors: Alberto Ruiz-Vela, Cucamonga; Maurice J. Brooks, Loma Linda; Douglas F. DeVries, Redlands, all of Calif.

[73] Assignee: Bear Medical Systems, Inc., Riverside, Calif.

[21] Appl. No.: 667,141

[22] Filed: Nov. 1, 1984

[51] Int. Cl.⁴ .............................................. G05D 11/02
[52] U.S. Cl. .................. 137/88; 128/204.22; 128/205.11
[58] Field of Search .................. 137/2, 3, 88, 93, 606, 137/625.4, 625.41, 624.11; 251/131; 128/204.21, 204.22, 205.11

[56] References Cited

U.S. PATENT DOCUMENTS

| | | | |
|---|---|---|---|
| 3,848,617 | 11/1974 | Dray | 137/606 X |
| 4,023,587 | 5/1977 | Dobritz | 137/88 |
| 4,072,148 | 2/1978 | Munson et al. | 128/142.2 |
| 4,112,885 | 9/1978 | Iwata | 251/131 X |
| 4,150,670 | 4/1979 | Jewett | 137/93 X |
| 4,204,536 | 5/1980 | Albarda | 128/204.22 |
| 4,345,612 | 8/1982 | Koni et al. | 137/101.19 |
| 4,506,642 | 3/1985 | Pfalzgraf | 251/131 X |

FOREIGN PATENT DOCUMENTS

| | | |
|---|---|---|
| 2373093 | 3/1978 | France . |
| 2026326 | 2/1980 | United Kingdom . |
| 2036565 | 7/1980 | United Kingdom . |
| 2099110 | 12/1982 | United Kingdom . |

Primary Examiner—Alan Cohan
Attorney, Agent, or Firm—Klein & Szekeres

[57] ABSTRACT

A gas blending system includes a proportional mixing valve having a valve element movable between first and second limits of travel corresponding to a minimum and maximum percentage, respectively, of one of the gases in the blended mixture. The position of the valve element is detected by a detection mechanism, producing a position signal inputted to a microcomputer. The microcomputer also receives a control signal representing a desired percentage of one of the gases to be blended. The microcomputer calculates a desired valving element position as a function of the value of the control signal, and generates a drive signal as a function of a comparison made by the microcomputer between the detected valve element position and the desired position. A motor drives the valve element to the desired position in response to the drive signal. The system also includes an accumulator for accumulating a selected volume of gas mixture flowing from the outlet of the valve prior to delivery of the mixture to a downstream demand. The accumulator increases the effective peak flow rate capacity of the system, while "smoothing out" instantaneous changes in downstream flow rate demand before the effects of such changes are experienced at the valve.

27 Claims, 4 Drawing Figures

ELECTRONICALLY-CONTROLLED GAS BLENDING SYSTEM

BACKGROUND OF THE INVENTION

The present invention relates generally to the field of gas blending apparatus. More particularly, this invention relates to a gas blending system in which a proportional blending valve is set and controlled electronically. The invention has specific applications in the medical field, especially in ventilators and anesthesia apparatus.

The precise blending of two or more gases is important in many applications, particularly in the medical field, where a precisely regulated mixture of gases must be administered to a patient. For example, in a ventilator or "respirator", it is usually desired to deliver a blend of oxygen-enriched air (i.e., more than 21 percent oxygen) to the patient being ventilated. Also, patients undergoing surgery under general anesthesia must be administered a precisely regulated mixture of anesthetic gas and respiratory gas (air, oxygen, or oxygen-enriched air). In either case, the proportional blend of gases must be set and maintained with accuracy.

A typical prior art blending system for a medical ventilator is disclosed in U.S. Pat. No. 4,072,148 to Munson, et al. In this prior art system, pressure-regulated air and oxygen are separately delivered to a mixing valve which is manually adjusted to achieve the desired proportional blend of the two gases. The valve itself has one flow path from an air inlet to a blended gas outlet, and another flow path from an oxygen inlet to the outlet. A valving element, the position of which is manually adjusted, opens one of the flow paths as it proportionately closes the other, thereby allowing the selection of a broad range of proportional air/oxygen blends.

While this system has achieved very satisfactory results, it does have some limitations. For example, the accuracy of the proportions of the blended gases, in terms of the variance of the actual proportions from their nominal values as set by the operator through the manual control, depends upon the accuracy of the calibration of the control dial or knob.

Another limitation stems from the need, in a medical ventilator, to accommodate a wide range of gas flow rates. Specifically, in a blending system using a mixing valve of fixed total flow area, the mixing accuracy depends on maintaining a balance in the regulated pressures of the gases entering the mixing valve. An imbalance in these pressures adversely affects the accuracy of the blending system. The error introduced by such imbalances is usually not significant at high flow rates, when the pressure drop across the mixing valve is considerably greater than the expected range of imbalance in the regulated gas pressures. At lower gas flow rates, however, the pressure drop across the valve decreases, and the effect of a regulated pressure imbalance becomes correspondingly more significant. On the other hand, if the flow rate is too high, the pressure drop across the valve is excessive, leaving inadequate gas pressure to overcome the pneumatic resistance of the ventilator so that gas can reach the patient.

Consequently, a gas blending valve with a fixed total flow orifice area is operative, with a suitable degree of accuracy, only within a relatively narrow range of flow rates. It has been found that the range of peak flow rates in an adult volume ventilator should be, advantageously, from about 5 liters per minute (1 pm) to about 150 1 pm, and perhaps higher. This range is too broad to be handled by a "single stage" mixing valve (that is, one having a single total flow orifice of fixed area, divided proportionately by the valving element). The prior art system described above approaches this problem by using a "multistage" mixing valve, in which the valve is divided into two or more valve "modules" characterized by progressively increasing volumetric flow capacities. As the flow rate increases, the higher flow capacity modules are sequentially opened, and as the flow rate decreases, they are sequentially closed. This structure allows the valve to operate throughout a very broad range of flow rates without degrading absolute mixing accuracy, as might occur by low flow rates through the higher capacity valve modules.

While multistage mixing valves can effectively broaden the range of flow rates accommodated by a gas blending system, they do so at the expense of increased mechanical complexity. In addition, even multistage valves can be subject to inaccuracies as a result of pressure transients generated upstream of the mixing valve by changes in downstream demand. In a medical ventilator, for example, rapid changes in delivered rates of gas flow due to instantaneous changes in the patient's demand for gas can be transmitted to the pressure regulation system too rapidly for compensation by the gas pressure regulators. The result is a pressure transient which causes a temporary imbalance in the regulated gas pressures, with a resultant deviation from the desired gas mixture.

Another approach to achieving higher accuracy in a gas blending system is exemplified by U.S. Pat. No. 4,345,612 to Koni, et al. This system employs an electrically-controlled "throttle" valve downstream from each gas regulator. Thus, both the pressure and flow rate of each gas to be blended are separately controlled before the gases are mixed in a manifold downstream from the outlets of the throttle valves. The flow rate through each throttle valve is measured by a flow rate sensor, which provides a feedback signal to the electronic circuitry which actuates the throttle valves.

The flow rate feedback feature of the Koni, et al. system provides an added degree of control, while the use of a separate electronically-controlled throttle valve for each gas provides an alternative approach (to multistage mixing valves) to broadening the useful flow rate range of the system. Nevertheless, this system is mechanically complex, as exemplified by its need for a separate throttle valve and flow rate sensor for each gas to be blended.

It can thus be appreciated that it would be highly desirable to provide a gas blending system which accommodates a wide range of flow rates without undue mechanical complexity, but which achieves, at the same time, accurate control of the gas blend. It would also be advantageous to provide in such a system the ability to mitigate the deleterious effects of downstream dynamic flow conditions, such as can be produced, in a ventilator, for example, by changes in patient demand.

SUMMARY OF THE INVENTION

Broadly, the present invention is a gas blending system comprising an electronically-controlled proportional mixing valve which is controlled by a microcomputer, and which includes an accumulator downstream from the valve to both broaden the operative flow rate range of the system, and to minimize the deleterious effects of pressure transients generated by dynamic flow conditions downstream from the valve.

In controlling the valve, the microcomputer receives a control or reference signal indicative of a selected proportional gas blend. From this signal, the microcomputer derives a value indicative of a desired valve position corresponding to the selected proportional gas blend. In a broad concept of the invention, a position sensor detects the actual position of the valve, and sends a position-indicative signal to the microcomputer. The microcomputer compares the value of the position-indicative signal with the calculated value indicative of the desired valve position. From this comparison, the microcomputer derives an output signal, the value of which is proportional to the positional relationship between the desired and actual valve positions. The output signal then is fed to a valve-driving device (e.g., a stepper motor), which adjusts the position of the valve to the desired position.

In a specific embodiment, the valve includes a valving element which is movable between a first limit of travel which minimizes the flow through a first flow path for a first gas to be blended, and a second limit of travel which minimizes the flow of a second gas to be blended through a second flow path. The valving element is moved to a desired position between the two limits of travel by a rotational shaft driven by a stepper motor. Carried on the shaft is an optically opaque element which blocks a first light beam at the first limit of travel and a second light beam at the second limit of travel. Blockage of either light beam changes the output signal of a photodetector, and this change in the output signal is transmitted to the microcomputer, which interprets the signal as indicating the presence of the valving element at one of the limits of travel.

The microcomputer has a memory in which is stored a "calibration curve". The calibration curve actually consists of a table of two sets of values. One set of values corresponds to selectable settings for the percentage of one of the two gases to be blended. The other set of values corresponds to positional relationships between each selectable valving element position and the first limit of travel of the valving element. There is a one-to-one correspondence between each value in the two sets. In other words, for each selectable gas percentage setting, there is a unique valving element position with respect to the first limit of travel.

In operation, an operator selects a desired percentage proportion of one of the gases to be blended. This percentage is transmitted as an input signal to the microcomputer, which responds by doing two things: (a) A signal is transmitted to appropriate drive circuitry for the stepper motor, whereby the motor is caused to drive the valving element to its first limit of travel; and (b) the memory is accessed to derive the valve element position value corresponding to the selected percentage value. When the microcomputer receives a signal from the appropriate photodetector indicating that the valving element has arrived at the first limit of travel, a second signal, proportional to the difference between the first limit of travel and the valve element position value derived from the calibration curve in the memory, is transmitted to the motor drive circuitry. The drive circuitry then actuates the motor to drive the valving element to the desired position, in which the volume rate of flow of the first gas is the selected percentage of the total blended gas volume rate of flow.

The blended gas, with the proper proportion (as a percentage of total gas flow) of the first gas, then flows out of the valve's outlet to an accumulator. The accumulator is simply a chamber of fixed volume having an inlet and an outlet. Two principal functions are performed by the accumulator. First, by providing a means for storing a volume of blended gas downstream from the mixing valve, the accumulator allows the system to accommodate higher peak flow rates than otherwise might be handled by a single stage mixing valve. Thus, the peak flow rate capacity of the system can be appreciably increased, until the stored volume in the accumulator is depleted, without resorting to multistage mixing valves. Second, the accumulator, with its stored volume of blended gas, acts as a pneumatic "filter" to "smooth out" instantaneous flow rate changes which can occur as a result of dynamic flow conditions downstream from the blending system. In a medical ventilator, for example, such dynamic flow conditions can result from sudden changes in the flow demands of the patient. Were it not for the ability of the stored volume of gas in the accumulator to accommodate these rapid flow rate changes, the instantaneous flow demand changes could be transmitted to the upstream (inlet) side of the mixing valve so rapidly that the pressure regulating system would have insufficient time to adjust, thereby causing variances in the regulated pressures of the incoming gases, with resultant errors in the blending proportions, as previously explained.

Although the blending system can be operated in an "open loop" fashion, as summarized above, as an option it can be configured to operate as a "closed loop" servo system. This can be accomplished in several ways. For example, a gas detector, sensitive to one of the blended gases, can be placed downstream from the mixing valve. The gas detector then transmits a signal, indicative of the concentration of the sensed gas, to the microcomputer, which then compares the gas detector signal with the operator-inputted signal indicating the desired gas concentration. As a result of the comparison, an error signal is produced which is inputted to the motor drive circuitry, so that the motor can be actuated to adjust the position of the valving element appropriately, until the error signal is minimized. Alternatively, a feedback signal can be derived from a continuous detection of the position of the valving element throughout its operating range. The value of the position-indicative feedback signal can then be compared, by the microcomputer, with the desired valving element position value derived from the stored calibration curve. By this comparison, an error signal is produced for adjustment of the position of the valving element through appropriate actuation of the motor.

The present invention offers several significant advantages over prior art gas blending systems. For example, the combination of the microcomputer, with its stored "calibration curve", and the means for detecting a "home" or "reference" position (i.e., the first limit of travel) for the valving element, allows precise regulation and control of the blended gas proportions, even in "open-loop" operation. With the addition of a downstream gas detector, even greater precision can be achieved through closed-loop servo operation. The use of an accumulator allows an extended flow rate range for the system, using only a single stage mixing valve, while also minimizing the deleterious effects of dynamic flow conditions downstream from the mixing valve.

Thus, the previously-mentioned shortcomings of the prior art are overcome using a system which is mechanically simple, and thus highly reliable in terms of its ability precisely to achieve and maintain a desired gas blend.

These and other advantages of the invention will be more fully appreciated from the detailed description which follows.

DETAILED DESCRIPTION OF THE INVENTION

A preferred embodiment of a gas blending system in accordance with the present invention is disclosed herein in the context of its use to blend air and oxygen in a pulmonary ventilation device. It should be noted at the outset, however, that, with minor modifications, the system can be used in other applications where other gases are to be blended. For example, in an anesthesia apparatus, the invention can be used to blend an anesthetic gas with a respiratory gas.

Figure 1:
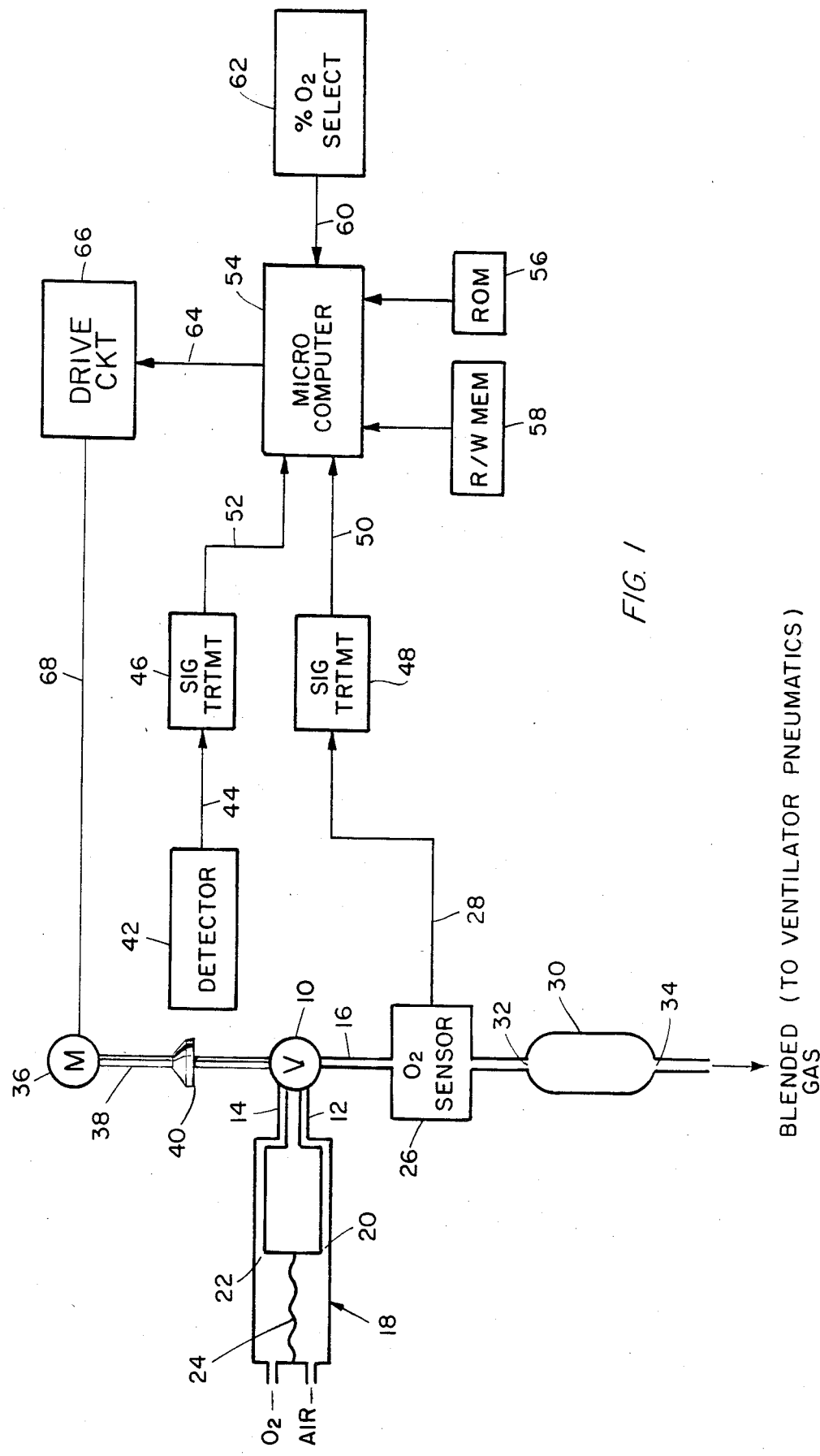
FIG. 1 is a schematic representation of a gas blending system in accordance with a preferred embodiment of the present invention.

Referring first to FIG. 1, the major elements of a preferred embodiment of the invention are illustrated in a schematic block diagram which shows their functional inter-relationships. At the heart of the system is a gas mixing valve 10 (to be described in greater detail below) which has an air inlet 12, an oxygen inlet 14, and a mixed gas outlet 16. The air and oxygen are received from pressure-regulated supplies (not shown), with the air and oxygen pressures regulated to be equal (within practically-obtainable tolerances). From their respective supplies, the air and oxygen are separately fed into a manifold 18 having separate air and oxygen flow paths 20,22, respectively. In the manifold 18, the flow paths 20,22 are in thermal communication with each other through a thermally conductive element, shown schematically in FIG. 1 and identified by the numeral 24. Ideally, the entire manifold 18 is of a thermally-conductive metal (e.g., aluminum) allowing efficient heat transfer between the two flow paths. The heat transfer allows the two gases to be of equal or nearly equal temperatures as they enter the valve inlets 12 and 14, thereby minimizing blending errors due to thermal gradients between the two inputted gases.

As will be described in further detail below, the mixing valve 10 has a first flow path from the air inlet 12 to the outlet 16, and a second flow path from the oxygen inlet 14 to the outlet. A single valving element proportionately closes one flow path as it opens the other. In this manner, while total gas flow through the outlet 16 remains substantially constant, the proportion of gas from one of the inlets can be varied from zero percent to 100 percent of the total gas flow, while the proportion of the other gas is varied in a complementary manner.

In the preferred embodiment illustrated in FIG. 1, blended gas from the valve outlet 16 flows through an oxygen sensor 26. The oxygen sensor 26 produces an output signal along line 28, which signal is indicative of the proportion of oxygen in the blended gas mixture.

Oxygen sensors which are suitable for use in a medical ventilator are well known in the art. See, for example, McPherson, S. P., *Respiratory Therapy Equipment* (2d Ed.), C. V. Mosby Co., 1981, pp. 153-160.

From the oxygen sensor 26, the blended gas enters an accumulator 30, which comprises a chamber of fixed volume having an inlet 32 and an outlet 34. Under conditions of low flow demand downstream from the accumulator, blended gas "accumulates" therein, reaching system pressure and becoming a stored volume. This storage action provides several advantages. First, during conditions of high downstream flow demand, the stored volume in the accumulator is extracted first and complements or augments the flow rate capacity of the mixing valve. This flow rate augmentation effectively increases the peak flow rate capacity of the mixing valve, until the stored volume is depleted. This allows a single stage valve to be used in many applications, instead of the previously-described "multistage" valves.

The stored volume of gas in the accumulator yields another advantage in that downstream flow demand is experienced at the accumulator before it is felt at the mixing valve. Thus, as previously mentioned, the volume in the accumulator is extracted first, before the demand is felt at the valve, thereby reducing the instantaneous flow demand imposed on the mixing valve and the pressure regulation system upstream from the valve. The accumulator, in effect, filters out or minimizes the instantaneous or sudden flow rate changes, created by downstream flow dynamics (e.g., changes in patient demand). Thus, such sudden flow rate changes are effectively isolated from the pressure regulation system, where the inability of the pressure regulation instantaneously to adjust to a changed flow rate could cause pressure imbalances which would create variations in the gas mixture.

Finally, the accumulator serves as a mixing chamber for the blended gases, providing a thorough "homogenization" of the gases before they enter the patient circuit.

The mixing valve 10 is driven by a stepper motor 36 via a rotational drive shaft 38. As will be described in further detail below, the shaft 38 is provided with a position-indicative element 40, the rotational position of which can be detected by a position detector 42, the latter generating a position indicative signal along a line 44. The position indicative element 40 and the position sensor 42 together form a system whereby the rotational position of the shaft with respect to a preselected reference position can be continuously sensed, or, alternatively, whereby the rotation of the shaft to such a reference position can be detected. In the preferred embodiment of the invention, the latter option is used. Specifically, as will be treated in greater detail below, the position sensing system 40,42 of preference in the present invention is one in which the detector 42 detects the position of the position-indicative element when the latter arrives at either of two preselected positions. Thus, the position-indicative signal on line 44 will indicate the arrival of the shaft at either one of the preselected positions.

The position-indicative signal is fed by the line 44 to signal treatment circuitry 46. This circuitry, of conventional design well-known in the art, includes circuitry for amplification, analog-to-digital conversion, and, possibly, linearization of the position-indicative signal. Similar signal treatment circuitry 48 treats the oxygen sensor output signal received from the line 28.

The amplified and digitized output signals from the oxygen sensor 26 and the position detector 42 are now inputted, via lines 50 and 52, respectively, into a microcomputer 54. The microcomputer 54 is of typical design, with a microprocessor, an input/output interface, and internal storage. The storage includes a Read Only Memory (ROM) 56 and a read/write memory 58. The ROM 56 contains the operational software for the microcomputer 54, as well as data which must be permanently stored. The read/write memory 58 may be used to store, temporarily, operator-inputted control signals, and the results of intermediate calculation steps, among other things.

Figure 4:
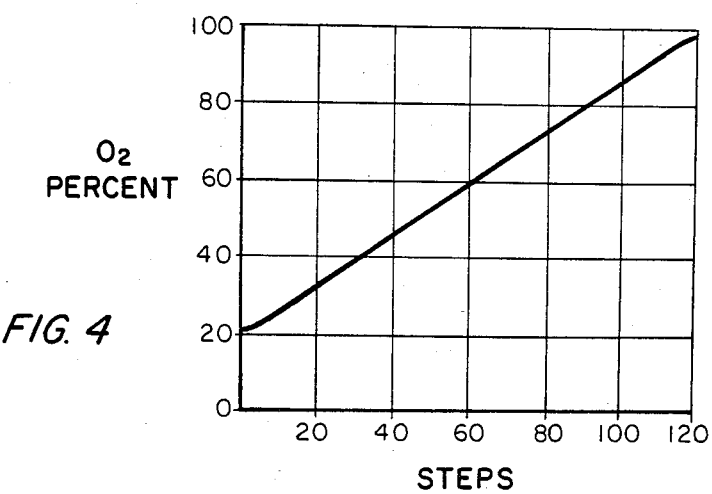
FIG. 4 is an idealized "calibration curve" of blended gas percentage as a function of stepper motor position, as employed by the microcomputer used in the present invention.

Among the data stored in the ROM 56 is that which may be referred to as a "calibration curve". In actuality, the calibration curve consists of a table having two sets of values. One set of values corresponds to selectable settings for the percentage of one of the two gases to be blended. The other set of values corresponds to a positional relationship (in terms of degrees of rotation of the drive shaft 38) between a selectable valving element position and one of the preselected reference positions. In a preferred embodiment of the invention, wherein the motor 36 used to drive the valve 10 is a stepper motor, the positional relationship may be expressed in the number of motor "steps" between the preselected reference position and a selectable valving element position. This relationship may be shown graphically, as in FIG. 4, which shows an exemplary "calibration curve", with oxygen percent expressed as a function of motor steps. It can be seen from FIG. 4 that there is a unique "positional relationship" value (expressed as a number of motor steps) associated with each selectable gas percentage setting. (The oxygen percentage value has a minimum of 21 percent, reflecting the proportion of oxygen in normal atmospheric air.)

The microcomputer 54 also receives a control signal, along the line 60, from a gas percentage selection control 62. In the specific embodiment described herein, the selection control 62 is set by the operator to a desired percentage of oxygen in the blended gas mixture. The operator setting causes the control signal, indicative of the desired oxygen percentage setting, to be inputted to the microcomputer. The microcomputer then calculates, from the calibration curve, the number of motor steps from the reference position to the position corresponding to the selected oxygen percentage setting. From the value of the position-indicative signal received from the position detector 42, the microcomputer can determine the actual positional relationship of the valve element (in terms of motor steps) with respect to the preselected reference position. By comparing the actual position of the valving element with the desired position (derived from the calibration curve), the microcomputer can generate an output signal having a value indicative of the number of steps through which the motor 36 must be driven to move the valving element to the position in which the selected oxygen percentage is blended into the gas mixture. This output signal is fed, over a line 64, first into appropriate drive circuitry 66, which includes amplification circuits, as is well known in the art. The drive circuitry 66 then produces a drive signal over a line 68 which feeds into the motor 36, so that the motor can be driven, in accordance with the microcomputer's instructions, to move the valving element to its selected position via the drive shaft 38.

As previously mentioned, the microcomputer receives an input signal, from the line 50, indicative of the percentage of oxygen in the blended gas mixture, as measured by the oxygen sensor 26. The value of this measure oxygen percentage signal is compared by the microcomputer with the value of the control signal received from the oxygen percentage selection control 62. The result of this comparison is an error signal, which is fed into the motor 36 via the line 64, the drive circuitry 66, and the line 68. By means of the error signal, the motor is actuated to adjust the valving element's position so as to minimize any variance between the measured oxygen percentage and the selected oxygen percentage, in the manner of a closed-loop servo system. It should be noted, however, that the closed loop servo operation may be needed only where extremely high accuracy is desired. In many applications, including the use of the present invention to blend oxygen and air in a respiratory ventilator, sufficient accuracy can be achieved in "open-loop" operation; that is, without the feedback signal provided by the oxygen sensor. Thus, the oxygen sensor and its associated closed-loop servo function should be considered optional.

The general principles of the invention having been explained, a specific preferred embodiment of the invention can now be described, with reference to FIGS. 2 and 3.

Figure 2:
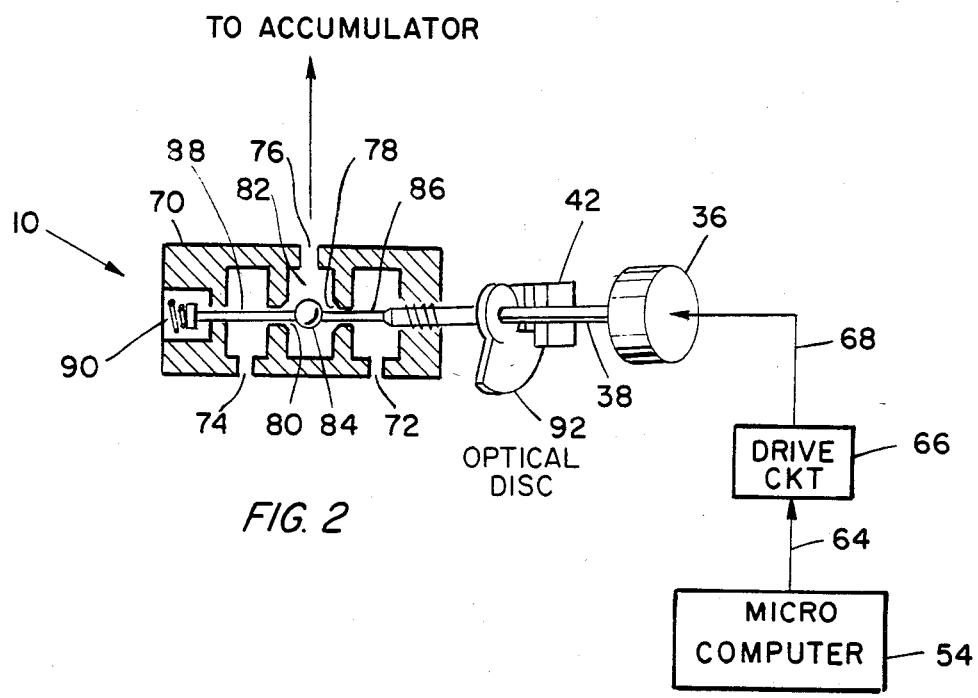
FIG. 2 is an idealized, semi-schematic representation of the mixing valve, position sensing mechanism, and stepper motor used in a preferred embodiment of the present invention.

FIG. 2 illustrates the mixing value 10 which may advantageously be used in the present invention. The value has a body 70 having an air inlet 72, an oxygen inlet 74, and blended gas outlet 76. The air and oxygen flow through separate valve seats (respectively numbered 78 and 80 in the drawing) into a total flow passage 82 leading to the outlet 76. A spherical valving element 84 is moved back and forth between the seats 78 and 80 by a shaft 86 which is threaded into the body 70 for axial movement therein as it is rotated. An axial pin 88, biased by a spring 90, engages the valving element 84 on the side diametrically opposed to the threaded shaft 86. The spring-loaded pin 88 assures a positive engagement between the valving element 84 and the threaded shaft 86, so that the valving element 84 will positively track the axial position of the threaded shaft 86.

The air inlet 72 and its associated valve seat 78 define an air flow path into the total flow passage 82, while the oxygen inlet 74 and its associated valve seat 80 define an oxygen flow path. As the valving element 84 is moved between the seats 78 and 80, the effective flow area of one of the seats is increased, while the effective flow area of the other is proportionately decreased. Thus, the flow rate capacity of the air flow path will be increased while that of the oxygen flow path is proportionately decreased, and vice versa. The total flow through the passage 82 into the outlet 76, however, remains constant regardless of the valving element position. In this manner, the percentage of oxygen in the total valve outlet flow of blended gas can be varied from a minimum of 21 percent (valve seat 78 totally open and valve seat 80 totally closed) to a maximum of 100 percent (valve seat 78 totally closed and valve seat 80 totally open).

As previously mentioned, the valving element is moved by a stepper motor 36 acting through a rotational drive shaft 38. The drive shaft 38, in turn, is connected to the threaded valve shaft 86 by a flexible coupling (not shown). In the illustrated preferred embodiment, the position indicator 40 carried on the drive shaft takes the form of a radially-extending, optically-opaque blade 92, as shown in FIGS. 2 and 3.

Figure 3:
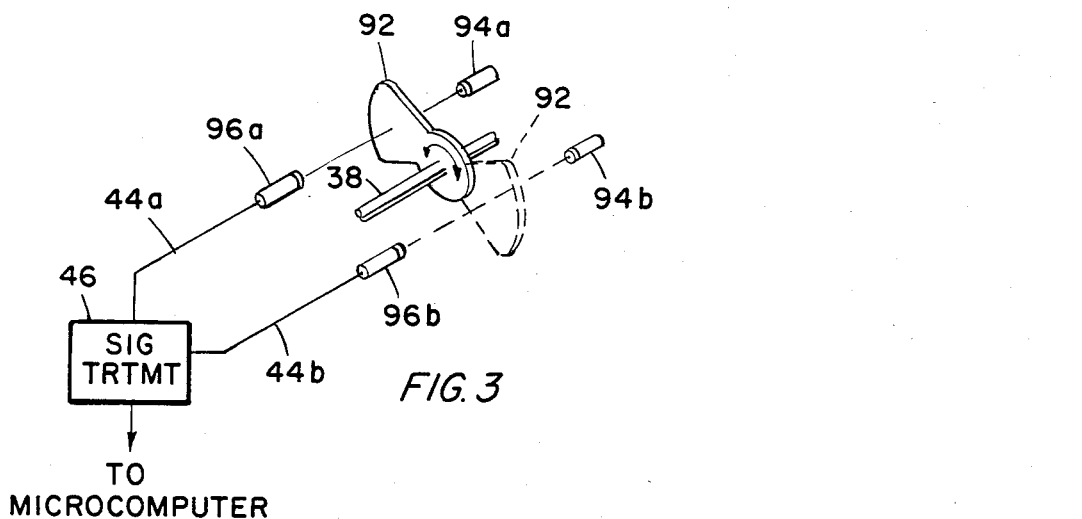
FIG. 3 is a detailed view of the position sensing mechanism shown in FIG. 2.

With specific reference to FIG. 3, the position detector 42, in a preferred embodiment, comprises first and second light beam sources 94a and 94b (which advantageously may be light-emitting diodes), and first and second photodetectors 96a and 96b, respectively receptive to the light beams generated by the light sources 94a and 94b. The photodetectors may be of any suitable type well known in the art, such as, for example, photodiodes, photoresistors, or phototransistors. In any case, the photodetectors 96a and 96b generate a signal having a first value when the light beam from the associated source is received, and a second value when no light from the source is received. The signals from the photodetectors 96a and 96b are transmitted, via lines 44a and 44b, respectively, to the signal treatment circuitry 46, as previously described, and then to the microcomputer 54.

The two light source/photodetector pairs 94a/96a, 94b96b are located on opposite sides of the drive shaft 38, with the blade 92 positioned so that at a first rotational reference position, it blocks the light beam from the source 94a, and at a second rotational reference position, it blocks the beam from the source 94b. Thus, the signals from the photodetectors 96a and 96b will indicate the arrival of the blade 92 at either of the rotational reference positions. In a preferred embodiment, the rotational reference positions are, advantageously, the first and second limits of drive shaft rotation, corresponding to the first and second limits, respectively, of axial travel of the valving element 84.

Referring once again to FIG. 1, the manner of operation of the specific preferred embodiment, described above and illustrated in FIGS. 2 and 3, will now be briefly explained.

When the operator sets the oxygen percentage selection control 62 to a desired oxygen percentage, the microcomputer 54 generates a "homing" signal to the motor 36 via the drive circuitry 66. This "homing" signal causes the motor 36 to rotate the drive shaft 38 to its first limit of travel, corresponding to the positioning of the valving element 84 against the oxygen flow path valve seat 80, thereby closing the oxygen flow path and allowing the total flow from the mixing value to be comprised of air (21 percent oxygen). With the shaft at this first limit of travel (which may now be considered its preselected rotational reference position), the position indicator 40 (actually, the blade 92) blocks the light beam from the light source 94a. The signal from the associated photodetector 96a thus changes value, indicating to the microcomputer that the valve element's first limit of travel (the "reference position") has been reached.

Next, the microcomputer derives, from the stored calibration curve, the stepper motor position (with respect to the first limit of travel "reference position") corresponding to the selected oxygen percentage value. An appropriate drive signal, having a value corresponding to the number of motor steps between the first limit of travel and the position derived from the calibration curve, is then transmitted to the motor. The motor responds by rotating the drive shaft 38 the appropriate number of "steps", whereby the valving element 84 is axially moved from the oxygen flow path valve seat 80 toward the air flow path valve seat 78 until the position corresponding to the desired oxygen proportion is reached. When the operator changes the selected oxygen percentage, another "homing" signal is generated, and the above-described process is repeated to move the valving element to a new position corresponding to the newly selected oxygen percentage.

As previously mentioned, at the drive shaft's second limit of travel, the blade 92 blocks the light beam from the second light source 94b, causing a change in the value of the output signal from the second photodetector 96b. This signal change is then transmitted to the microcomputer, which responds by generating an output signal which commands the motor to stop, thereby preventing the motor from attempting to drive the valving element past its second limit of travel. The motor may also then be commanded to reverse direction. This may be particularly advantageous if an "auto-verification" mode is used. In such a mode, the motor is caused, by the microcomputer, to respond to any change in the oxygen percentage setting by turning first to the second limit of travel before it "homes" to the first limit of travel. The microcomputer can then count the number of motor "steps" between the two limits of travel, and then compare the counted number with a preselected reference number. If there is a variance between these two numbers, the microcomputer will assume that something has occurred to compromise the accuracy of the system (e.g., damage to the valve components or motor), and an appropriate alarm will be activated.

Of course, as previously discussed, the oxygen sensor 26 may optionally be added to the system to provide closed loop servo control, in the manner described above.

Although a specific embodiment has been described herein as a preferred embodiment, it will be appreciated that a number of modifications, within the spirit and scope of the invention, will suggest themselves to those of requisite skill in the pertinent arts. Thus, various means can be used to detect the position of the valving element, either directly, or indirectly (as done in the preferred embodiment, by detecting the rotational position of the drive shaft). For example, the position detector 42 can respond to varying magnetic or electrical fields as a function of valve element position or drive shaft rotational position. Position detectors of such types are known in the art. See, for example, U.S. Pat. No. 4,204,536 to Albarda. Also, the position sensing system can be modified to provide a continuous position-indicative signal; that is, one which indicates (directly or indirectly) the valve element position throughout its range of travel. Such a modification of the embodiment described herein would entail the use, for example, of an element on the drive shaft which transmits an amount of light that varies as a known function of its rotational position with respect to an axially-oriented light beam. The use of such a continuous position detector would allow the position detector itself to generate a feedback signal for closed loop servo operation, thereby possibly obviating the need for an oxygen sensor to provide the same function.

It can thus be seen that the present invention provides several advantages over the prior art gas blending systems. Specifically, the use of the accumulator provides an extended peak flow rate capacity without mechanical complexity, thorough mixing of the blended gases, and stability in the selected blend proportions through minimization of pressure transients. Furthermore, the microcomputer control of the mixing valve, with a position-indicative signal as a control parameter, offers a high degree of accuracy and stability, with or without closed loop servo control. Moreover, the microcomputer control provides the flexibility required to accommodate closed loop servo operation, where needed or desired, with a minimum of additional hardware.

What is claimed is:

1. A system for proportionately blending a mixture of at least two different gases, comprising:
   a valve body having a first inlet for a first gas, a second inlet for a second gas, an outlet, a first flow path from said first inlet to said outlet, and a second flow path from said second inlet to said outlet;
   a valving element movable within said valve body to proportionately open one of said first and second flow paths while simultaneously proportionately closing the other, whereby the total gas flow rate through said outlet is substantially independent of the position of said valving element, said valving element having a first limit of travel which provides a minimum selectable flow rate through said first flow path and a second limit of travel which provides a minimum selectable flow rate through said second flow path;
   first means for selecting a desired proportion for said first gas in said mixture and producing a proportion signal having a value indicative of said desired proportion;
   second means for electronically storing a previously-calculated calibration curve consisting of a value indicative of a unique valving element position with respect to said first limit of travel for each of a number of selectable values for said proportion signal;
   third means for detecting the presence of said valving element at said first limit of travel and producing a position signal indicative of the presence of said valving element at said first limit of travel;
   fourth means, responsive to said second means, said proportion signal and said position signal, for (a) deriving from said calibration curve the valving element position value corresponding to the value of said proportion signal, (b) generating a homing signal in response to a change in value of said proportion signal, and (c) generating a drive signal having a value indicative of the valving element position value derived from said calibration curve; and
   fifth means, responsive to said homing signal and said drive signal, for (a) driving said valving element to said first limit of travel in response to said homing signal, and (b) driving said valving element from said first limit of travel to a position corresponding to said derived valving element position value in response to said drive signal;
   whereby said position of said valving element corresponding to said derived valving element position value produces substantially said desired proportion of said first gas in said mixture.

2. The system of claim 1, further comprising:
   accumulator means, in fluid communication with said valve outlet, for accumulating a selected volume of gas mixture flowing from said valve outlet, said accumulator means including (a) means for receiving the flow of said mixture from said valve outlet, and (b) means for discharging all or part of said accumulated volume of gas mixture in response to a downstream demand.

3. The system of claim 1, further comprising:
   a first conduit for conducting said first gas from a first source to said first inlet;
   a second conduit for conducting said second gas from a second source to said second inlet; and
   temperature equalizing means, operatively associated with said first and second conduits, for allowing passive thermal transfer between said first and second gases as they flow through said first and second conduits, respectively.

4. The system of claim 2, further comprising:
   sixth means, fluidly communicating with said outlet, for measuring the proportion of a selected one of said gases in said mixture of gases flowing from said outlet and producing a feedback signal having a value which is indicative of the measured proportion of said selected gas;
   seventh means, responsive to said feedback signal and said proportion signal, for generating an error signal indicative of the deviation of said measured proportion from said desired proportion; and
   eighth means for applying said error signal to said fifth means, thereby adjusting the position of said valving element in proportion to the value of said error signal.

5. The system of claim 1, wherein said valving element is moved between said first and second limits of travel by a rotational drive shaft driven by said fifth means, and wherein said third means comprises:
   position detection means, operatively associated with said drive shaft, for detecting the presence of said drive shaft at a preselected rotational reference position corresponding to said first limit of travel of said valving element.

6. The system of claim 5 wherein said position detection means comprises:
   a source of a light beam;
   a photodetector positioned to receive said light beam; and
   an optically-opaque element positioned on said drive shaft so as to block said light beam when said drive shaft is rotated to said preselected rotational reference position;
   whereby said photodetector generates said position signal when said light beam is blocked.

7. The system of claim 6, wherein said fifth means is a stepper motor having a known number of steps between first and second preselected rotational reference positions, and said drive shaft has first and second rotational reference positions corresponding to said first and second rotational reference positions of said motor, respectively, and to said first and second limits of travel, respectively, of said valving element.

8. The system of claim 7, wherein each of said valving element position values in said calibration curve corresponds to a unique number of stepper motor steps from said first preselected reference position for each of said selectable proportion signal values.

9. The system of claim 1, wherein said fifth means responds to said homing signal by driving said valving element first to said second limit of travel and then to said first limit of travel; wherein said third means detects the arrival of said valving element at said second and first limits of travel and produces said position signal having values indicative of the presence of said valving element at said second and first limits of travel;

and wherein said fourth means responds to the values of said position signal indicative of the presence of said valving element at said limits of travel by (a) calculating the actual positional relationship between said first and second limits of travel, and (b) comparing said actual positional relationship between said limits of travel with a preselected reference value for said positional relationship.

10. A system for proportionately blending a mixture of at least two different gases, comprising:

a valve body having a first inlet for a first gas, a second inlet for a second gas, an outlet, a first flow path from said first inlet to said outlet, and a second flow path from said second inlet to said outlet;

a valving element movable within said valve body to proportionately open one of said first and second flow paths while simultaneously proportionately closing the other, whereby the total gas flow rate through said outlet is substantially independent of the position of said valving element, said valving element having a first limit of travel which provides a minimum selectable flow rate through said first flow path and a second limit of travel which provides a minimum selectable flow rate through said second flow path;

first means for selecting a desired proportion for said first gas in said mixture and producing a proportion signal having a value indicative of said desired proportion;

second means for electronically storing a previously-calculated calibration curve consisting of a value indicative of a unique valving element position with respect to said first limit of travel for each of a number of selectable values for said proportion signal;

third means for detecting the position of said valving element with respect to said first limit of travel and producing a position signal having a value indicative of the actual position of said valving element with respect to said first limit of travel;

fourth means, responsive to said second means, said proportion signal, and said position signal, for (a) deriving from said calibration curve the valving element position value corresponding to the value of said proportion signal, (b) comparing said derived valving element position value with the value of said position signal, and (c) generating a drive signal as a function of the outcome of said comparison;

fifth means, responsive to said drive signal, for driving said valving element to the position corresponding to the valving element position value derived from said calibration curve; and sixth means, in fluid communication with said valve outlet, for accumulating a selected volume of gas mixture flowing from said valve outlet, said sixth means including (a) means for receiving the flow of said mixture from said valve outlet, and (b) means for discharging all or part of said accumulated volume of gas mixture in response to a downstream demand.

11. The system of claim 10, wherein said third means detects the presence of said valving element at said first limit of travel and produces a position signal indicative of the presence of said valving element at said first limit of travel; said fourth means generates a homing signal in response to a change in value of said proportion signal; said drive signal has a value indicative of the valving element position value derived from said calibration curve; and said fifth means responds to said homing signal and said drive signal, by (a) driving said valving element to said first limit of travel in response to said homing signal, and (b) driving said valving element from said first limit of travel to a position corresponding to said derived valving element position value in response to said drive signal.

12. The system of claim 10, further comprising:

seventh means, fluidly communicating with said valve outlet, for measuring the proportion of a selected one of said gases in said mixture of gases flowing from said outlet and producing a feedback signal having a value which is indicative of the measured proportion of said selected gas;

eighth means, responsive to said feedback signal and said proportion signal, for generating an error signal indicative of the deviation of said measured proportion from said desired proportion; and ninth means for applying said error signal to said fifth means, thereby adjusting the position of said valving element in proportion to the value of said error signal.

13. The system of claim 11, wherein said valving element is moved between said first and second limits of travel by a rotational drive shaft driven by said fifth means, and wherein said third means comprises:

position detection means, operatively associated with said drive shaft, for detecting the presence of said drive shaft at a preselected rotational reference position corresponding to said first limit of travel of said valving element.

14. The system of claim 13, wherein said position detection means comprises:

a source of a light beam;

a photodetector positioned to receive said light beam; and an optically-opaque element positioned on said drive shaft so as to block said light beam when said drive shaft is rotated to said preselected rotational reference position;

whereby said photodetector generates said position signal when said light beam is blocked.

15. The system of claim 14, wherein said fifth means is a stepper motor having a known number of steps between first and second preselected rotational reference positions, and said drive shaft has first and second rotational reference positions corresponding to said first and second rotational reference positions of said motor, respectively, and to said first and second limits of travel, respectively, of said valving element.

16. The system of claim 15, wherein each of said valving element position values in said calibration curve corresponds to a unique number of stepper motor steps from said first preselected reference position for each of said selectable proportion signal values.

17. The system of claim 11, wherein said fifth means responds to said homing signal by driving said valving element first to said second limit of travel and then to said first limit of travel; wherein said third means detects the arrival of said valving element at said second and first limits of travel and produces said position signal having values indicative of the presence of said valving element at said second and first limits of travel; and wherein said fourth means responds to the values of said position signal indicative of the presence of said valving element at said limits of travel by (a) calculating the actual positional relationship between said first and second limits of travel, and (b) comparing said actual positional relationship between said limits of travel with a preselected reference value for said positional relationship.

18. A system for proportionately blending a mixture of at least two different gases, comprising:
  a valve body having a first inlet for a first gas, a second inlet for a second gas, an outlet, a first flow path from said first inlet to said outlet, and a second flow path from said second inlet to said outlet;
  a valving element movable within said valve body to proportionately open one of said first and second flow paths while simultaneously proportionately closing the other, whereby the total gas flow rate through said outlet is substantially independent of the position of said valving element, said valving element having a first limit of travel which provides a minimum selectable flow rate through said first flow path and a second limit of travel which provides a minimum selectable flow rate through said second flow path;
  first means for selecting a desired proportion for said first gas in said mixture and producing a proportion signal having a value indicative of said desired proportion;
  second means for electronically storing a previously-calculated calibration curve consisting of a value indicative of a unique valving element position with respect to said first limit of travel for each of a number of selectable proportion-indicative values for said proportion signal;
  third means for detecting the position of said valving element with respect to said first limit of travel and producing a position signal having a value indicative of the actual position of said valving element with respect to said first limit of travel;
  fourth means, responsive to said second means, said proportion signal, and said position signal, for (a) deriving from said calibration curve a desired valving element position value corresponding to the value of said proportion signal, (b) comparing said derived valving element position value with the value of said position signal, and (c) generating a drive signal as a function of the outcome of said comparison; and
  fifth means, responsive to said drive signal, for driving said valving element to the desired valving element position corresponding to the valving element position value derived from said calibration curve.

19. The system of claim 18, further comprising:
  sixth means, fluidly communicating with said outlet, for measuring the concentration of a selected one of said gases in said mixture of gases flowing from said outlet and producing an output signal having a value which is indicative of the measured concentration of said selected gas;
  seventh means for generating a reference signal having a value which is indicative of a desired concentration of said selected gas;
  eighth means, responsive to said output signal and said reference signal, for generating an error signal indicative of the deviation of said measured concentration from said desired concentration; and
  ninth means for applying said error signal to said fifth means, thereby adjusting the position of said valving element in proportion to the value of said error signal.

20. The system of claim 18, further comprising:
  referencing means, responsive to said proportion signal, for generating a reference signal having a value which is indicative of a desired position for said valving element corresponding to said desired proportion;
  error signal generating means, responsive to said position signal and said reference signal, for generating an error signal having a value indicative of the deviation between said actual position and said desired position of said valving element; and
  means for applying said error signal to said fifth means, thereby adjusting the position of said valving element in proportion to the value of said error signal.

21. The system of claim 18, further comprising:
  accumulator means, downstream from said outlet, for (a) accumulating a selected volume of gas mixture flowing from said outlet, and (b) discharging at least some of said accumulated volume in response to a downstream demand.

22. The system of claim 18, wherein said fifth means is operatively connected to said valving element by a rotational drive element, and wherein said third means comprises:
  position indicating means on said drive element for indicating the rotational position of said drive element with respect to a preselected reference position; and
  detection means responsive to the rotational position of said position indicating means, for generating said position signal.

23. The system of claim 22, wherein said position indicating means includes an optically-opaque, radially-extending blade on said drive element, and said detection means includes a photodetector and a light source, whereby said blade occludes the path of light from said source to said photodetector when said drive element is rotated to said reference position.

24. The system of claim 18, wherein said fourth means responds to a change in the value of said proportion signal by producing a homing signal; said fifth means responds to said homing signal by driving said valving element to said first limit of travel; said third means detects the arrival of said valving element at said first limit of travel; said position signal indicates the presence of said valving element at said first limit of travel; and said fourth means responds to the value of said position signal indicating the presence of said valving element at said first limit of travel by calculating the positional relationship between said desired valving element position and said first limit of travel;
  whereby said fifth means further responds to said drive signal by driving said valving element from said first limit of travel to said desired position.

25. The system of claim 24, wherein said fifth means responds to said homing signal by driving said valving element first to said second limit of travel and then to said first limit of travel; said third means detects the arrival of said valving element at said second and first limits of travel and produces said position signal having values indicative of the presence of said valving element at said second and first limits of travel; and wherein said fourth means responds to the values of said position signal indicative of the presence of said valving element at said limit of travel by (a) calculating the actual positional relationship between said first and second limits of travel, and (b) comparing said actual positional relationship between said limits of travel with a preselected reference value for said positional relationship.

26. The system of claim 18, wherein said fifth means comprises:
- a stepper motor having a known number of steps between first and second preselected rotational positions;
- a rotational drive shaft driven by said stepper motor between said first and second preselected rotational positions; and
- means, operatively connecting said drive shaft to said valving element, for driving said valving element between said first limit of travel, when said drive shaft is at said first preselected rotational position, and said second limit of travel, when said drive shaft is at said second preselected rotational position.

27. The system of claim 26, wherein said calibration curve consists of a value indicative of a unique number of stepper motor steps from said first preselected rotational position for each of said selectable proportion-indicative values, and said calculation means calculates a desired rotational position with respect to said first preselected rotational position from the value of said proportion signal and the corresponding stepper motor step value from said calibration curve; whereby said proportion signal has a value indicative of said desired rotational position; and said third means detects the actual rotational position of said drive shaft with respect to said first preselected rotational position and produces said position signal with a value indicative of said actual rotational position.

* * * * *